US012766217B2

(12) United States Patent
Zeng et al.

(10) Patent No.: US 12,766,217 B2
(45) **Date of Patent: *Oct. 20, 2026**

(54) EMBOLIC MICROSPHERES

(71) Applicant: Varian Medical Systems, Inc., Palo Alto, CA (US)

(72) Inventors: Hongxia Zeng, Maple Grove, MN (US); Bruce R. Forsyth, Hanover, MN (US); Hong Cao, Maple Grove, MN (US); Matthew R. DeWitt, Charlottesville, VA (US); Heidi Schwanz, Maple Grove, MN (US)

(73) Assignee: Varian Medical Systems, Inc., Palo Alto, CA (US)

(*) Notice: Subject to any disclaimer, the term of this patent is extended or adjusted under 35 U.S.C. 154(b) by 202 days.

This patent is subject to a terminal disclaimer.

(21) Appl. No.: 17/557,175

(22) Filed: Dec. 21, 2021

(65) Prior Publication Data

US 2022/0111114 A1 Apr. 14, 2022

Related U.S. Application Data

(63) Continuation of application No. 16/033,303, filed on Jul. 12, 2018, now Pat. No. 11,235,084.

(60) Provisional application No. 62/531,956, filed on Jul. 13, 2017.

(51) Int. Cl.

| | |
|---|---|
| ***A61L 24/02*** | (2006.01) |
| ***A61K 9/00*** | (2006.01) |
| ***A61K 9/16*** | (2006.01) |
| ***A61L 24/00*** | (2006.01) |
| ***A61L 24/04*** | (2006.01) |
| ***A61L 24/06*** | (2006.01) |
| *A61M 25/00* | (2006.01) |

(52) U.S. Cl.

CPC ............ *A61L 24/02* (2013.01); *A61K 9/0019* (2013.01); *A61K 9/1617* (2013.01); *A61K 9/1623* (2013.01); *A61L 24/0015* (2013.01); *A61L 24/0031* (2013.01); *A61L 24/0042* (2013.01); *A61L 24/043* (2013.01); *A61L 24/046* (2013.01); *A61L 24/06* (2013.01); *A61L 2300/604* (2013.01); *A61L 2300/608* (2013.01); *A61L 2400/06* (2013.01); *A61L 2420/06* (2013.01); *A61L 2420/08* (2013.01); *A61L 2430/36* (2013.01); *A61M 25/0097* (2013.01)

(58) Field of Classification Search

CPC ............. A61M 25/0097; A61K 9/0019; A61K 9/1623; A61K 9/1617; A61L 24/02; A61L 24/0015; A61L 24/0042; A61L 24/0031; A61L 24/043; A61L 24/046; A61L 24/06; A61L 2300/604; A61L 2300/608; A61L 2400/06; A61L 2420/06; A61L 2420/08; A61L 2430/36

See application file for complete search history.

(56) References Cited

U.S. PATENT DOCUMENTS

| | | | | |
|---|---|---|---|---|
| 6,545,097 B2 | 4/2003 | Pinchuk et al. | | |
| 7,727,555 B2 | 6/2010 | DiCarlo et al. | | |
| 7,736,671 B2 | 6/2010 | DiCarlo et al. | | |
| 8,246,998 B2 * | 8/2012 | O'Gara | ................ | A61K 9/0024 424/501 |
| 11,235,084 B2 * | 2/2022 | Zeng | .................... | A61K 9/1617 |
| 2004/0208845 A1 | 10/2004 | Michal et al. | | |
| 2005/0095428 A1 | 5/2005 | Dicarlo et al. | | |
| 2005/0149173 A1 | 7/2005 | Hunter et al. | | |
| 2009/0117033 A1 | 5/2009 | O'Gara | | |
| 2012/0288441 A1 | 11/2012 | O'Gara | | |
| 2013/0323306 A1 | 12/2013 | Weber | | |

FOREIGN PATENT DOCUMENTS

| | | | |
|---|---|---|---|
| CN | 1596127 | A | 3/2005 |
| CN | 1747721 | A | 3/2006 |
| CN | 101321542 | A | 12/2008 |
| CN | 101820861 | A | 9/2010 |
| CN | 103536973 | A | 1/2014 |
| CN | 104258474 | A | 1/2015 |
| CN | 104271171 | A | 1/2015 |
| CN | 106332213 | A | 1/2017 |
| CN | 106334213 | A | 1/2017 |
| CN | 106512015 | A | 3/2017 |
| WO | 03030941 | A1 | 4/2003 |
| WO | 2004071495 | A1 | 8/2004 |
| WO | 2009014549 | A1 | 1/2009 |
| WO | 2011066379 | A2 | 6/2011 |

OTHER PUBLICATIONS

Sibylle Stampfl, et al, Biocompatibility and Recanalization Characteristics of Hydrogel Microspheres with Polyzene-F as Polymer Coating, 31 Cardiovasc. Intervent. Radiol. 799 (Year: 2008).*
Ming Chao, et al, A Nonrandomized Cohort and a Randomized Study of Local Control of Large Hepatocarcinoma by Targeting Intratumoral Lactic Acidosis, 5 eLife e 1561 (Year: 2016).*
First Examination Report dated May 28, 2021, in CN Application No. Chinese Application, No. 201880046400.
International Search Report and Written Opinion for PCT Application No. PCT/US2018/041732 mailed on Oct. 11, 2018, 9 pages.

(Continued)

*Primary Examiner* — Sean M Basquill
(74) *Attorney, Agent, or Firm* — Morgan, Lewis & Bockius LLP; Manita Rawat

(57) ABSTRACT

In some aspects, the disclosure pertains to injectable particles that contain at least one pH-altering agent that is configured to be released from the injectable particles in vivo, upon embolization of an intratumoral artery of a tumor with the injectable particles. In certain instances, the pH altering agent may be a basic agent having a pH value of 7.5, a buffering agent having a pKa value of 7.6 or more, or both. Other aspects of the disclosure pertain to preloaded containers containing such injectable particles and methods of using such injectable particles.

17 Claims, No Drawings

(56) References Cited

OTHER PUBLICATIONS

Stampfl, et al., "Biocompatibility and Recanalization Characteristics of Hydrogel Microspheres with Polyzene-F as Polymer Coating" 2008, Cardiovasc. Intervent. Radiol., 31: 799-806.
M. Chao, et al., "A nonrandomized cohort and a randomized study of local control of large hepatocarcinoma by targeting intratumoral lactic acidosis", eLife, (2016), pp. 1-18.
J. Xie, et al, "Beyond Warburg effect—dual metabolic nature of cancer cells", Scientific Reports, (2014), pp. 1-12.
H. Wu, et al, "Central role of lactic acidosis in cancer cell resistance to glucose deprivation-induced cell death", Journal of Pathology, (2012), pp. 1-11.
Second Office Action dated Mar. 2, 2022, in CN Application No. Chinese Application, No. 201880046400.2, 14 pages.
Extended European Search Report for European Patent Application No. 23171684.6 issued May 5, 2023, 6 pages.

* cited by examiner

EMBOLIC MICROSPHERES

CROSS-REFERENCE TO RELATED APPLICATIONS

This application is a continuation application of U.S. patent application Ser. No. 16/033,303, entitled "Embolic Microspheres," filed on Jul. 12, 2018 that claims the benefit of U.S. Provisional Application No. 62/531,956, entitled "Embolic Microspheres," filed Jul. 13, 2017, the disclosures of which are each hereby incorporated by reference in their entireties.

BACKGROUND

Many clinical situations benefit from regulation of the vascular, lymphatic or duct systems by restricting the flow of body fluid or secretions. For example, the technique of embolization involves the introduction of particles into the circulation to occlude blood vessels, for example, so as to either arrest or prevent hemorrhaging or to cut off blood flow to a structure or organ as a means to restrict necessary oxygen and nutrients to the targeted tissue. Permanent or temporary occlusion of blood vessels is desirable for managing various diseases and conditions.

In a typical embolization procedure, local anesthesia is first given over a common artery. The artery is then percutaneously punctured and a catheter is inserted and fluoroscopically guided into the area of interest. An angiogram is then performed by injecting contrast agent through the catheter. Embolic particles are then deposited through the catheter. The embolic particles are chosen, for example, based on the size of the vessel to be occluded, the desired duration of occlusion, and/or the type of disease or condition to be treated, among others factors. A follow-up angiogram is usually performed to determine the specificity and completeness of the arterial occlusion.

Various polymer-based microspheres are currently employed to embolize blood vessels. These microspheres are usually introduced to the location of the intended embolization through microcatheters. Many commercially available embolic microspheres are composed of polymers. Materials commonly used commercially for this purpose include polyvinyl alcohol (PVA), including acetalized PVA (e.g., Contour SE™ embolic agent, Boston Scientific, Natick, Mass., USA) and crosslinked acrylic hydrogels (e.g., Embosphere® Microspheres, embolic microspheres formed from tris-acyl cross-linked with gelatin, commercially available from Merit Medical Systems, Inc. (South Jordan, Utah, USA). Similar microspheres have been used in chemoembolization to increase the residence time of the therapeutic after delivery. In one specific instance, a therapeutic agent (doxorubicin) has been directly added to polyvinyl alcohol hydrogel microspheres such that it can be released locally after delivery (e.g., DC Bead™ drug delivery chemoembolization system, Biocompatibles International plc, Farnham, Surrey, UK). Further examples of embolic microspheres include embolic microspheres having hydrogel cores (e.g., containing a methyl methacylate polymer) coated with Polyzene®-F (poly[bis(trifluroethoxy)phosphazene]), commercially available from CeloNova BioSciences (San Antonio, Tex.) under the name Embozene®, embolic microspheres containing acrylamide PVA polymers, commercially available from Biocompatibles International (Oxford, Conn.) under the name Bead Block™, and embolic microspheres containing a PVA-Sodium acrylate copolymer, commercially available from Merit Medical Systems, Inc. (South Jordan, Utah, USA) under the name QuadraSphere®. Still other examples of commercially available microspheres include glass microspheres with entrapped radioisotopes (e.g., $^{90}Y$), in particular, TheraSpheres™, MDS Nordion, Ottawa, Canada and polymer microspheres that contain monomers that are capable of chelating radioisotopes ($^{90}Y$), in particular, SIR-Spheres®, SIRTex Medical, New South Wales, Australia.

Embolic particles have been used in bland transarterial embolization (TAE) and transarterial chemoembolization (TACE). The goal of TACE or TAE procedures is to controllably embolize a local tumor microenvironment, effectively starving the tumor cells by removing an upstream source of oxygen and glucose. However, tumor progression is known to lead to intratumoral lactic acidosis as a byproduct of the Warburg effect and high levels of hypoxia. It has been postulated that TACE or TAE can increase hypoxia and the inability to flush lactic acid out of the tumor and that, ultimately, this localization of a high concentration of lactic acidosis decreases glycolysis rate, reducing the efficacy of TACE or TAE by transforming cancer cells to a dormant state, by arresting cells at the G0/G1 phase, and by reducing their dependence on glucose. See, e.g., Chao et al., "A nonrandomized cohort and a randomized study of local control of large hepatocarcinoma by targeting intratumoral lactic acidosis," *Elife,* 2016 Aug. 2;5. pii: e15691. doi: 10.7554/eLife.15691. In other words, lactic acidosis which is commonly present in the tumor and can be potentially exacerbated by TAE or TACE treatment, effectively protects cancer cells against glucose starvation. It has been further postulated that this protective function relies on co-presence of lactate and hydrogen ions, and that removing either of these would eliminate this function. Id. See also Jiansheng Xie et al., "Beyond Warburg effect—dual metabolic nature of cancer cells," *Scientific Reports,* 4: Article number: 4927 (2014), DOI: 10.1038/srep04927 and Hao Wu et al., "Central role of lactic acidosis in cancer cell resistance to glucose deprivation-induced cell death," *J Pathol.* 2012 June;227 (2):189-99. doi: 10.1002/path.3978. A recently developed procedure has been shown to improve clinical outcome for liver cancer patients, with better cell response and patient survival rates being observed. Chao et al., supra. During this procedure, 5% sodium bicarbonate was infused alternatively with doxorubicin-lipiodol emulsion and oxaliplatin/homocamptothecin with the dose adjusted to tumor size, after which the artery was permanently embolized with PVA (Embosphere® Microspheres) and microcoil (Tornado, COOK Medical, USA). Id.

There is a continuing need in the art for improved injectable particles as well as methods of treatment using the same to result in localized modification of the tumor microenvironment to increase the efficacy of the glucose and oxygen limiting therapy.

SUMMARY

In accordance with some aspects, the present disclosure pertains to injectable particles that comprise at least one pH-altering agent that is configured to be released from the injectable particles in vivo upon embolization of an intratumoral artery of a tumor with the injectable particles.

In various embodiments, the injectable particles may be spherical or non-spherical particles, and the injectable particles may range from 20 microns (μm) or less to 5000 microns or more in diameter.

In various embodiments, which may be used in conjunction with any of the preceding aspects and embodiments, the injectable particles may be configured such that, upon ern-bolization of the intratumoral artery of the tumor with the injectable particles, the injectable particles release the pH-altering agent such that a microenvironment is created in a vascular bed of the tumor downstream of the injectable particles, which has a pH that is higher than a pH that would otherwise exist in the absence of the pH-altering agent (e.g., upon embolization with injectable particles of the same composition, except with the pH-altering agent removed). Such a higher pH microenvironment may be maintained for at least 1 hour up to 8 weeks or more, for example, ranging from 1 hour to 4 hours to 12 hours to 1 day to 2 days to 4 days to 1 week to 2 weeks to 4 weeks to 8 weeks (Le., ranging between any two of the preceding numerical values), in some instances, ramping from 2 to 4 weeks.

In various embodiments, which may be used in conjunction with any of the preceding aspects and embodiments, the pH-altering agent may be a basic agent having a pH value (e.g., at pH value at 100 mM concentration in water at 25° C.) of 7.5 or more, in certain instances, ranging from 7.5 to 10.0.

In various embodiments, which may be used in conjunction with any of the preceding aspects and embodiments, the pH-altering anent may be a buffering anent having a pKa value (e.g., a pKa value extrapolated to infinite dilution (buffer concentration=0) in water at 25° C., also referred to as a pKa° value) of 7.6 or more, in certain instances ranging from 7.6 to 35.

In various embodiments, which may be used in conjunction with any of the preceding aspects and embodiments, the pH-altering agent may be an organic compound (e.g., an organic amine, a zwitterionic organic compound, among many others) or an inorganic compound (e.g., a carbonate, phosphate, phosphazene, among many others).

In various embodiments, which may be used in conjunction with any of the preceding aspects and embodiments, the pH-altering agent may be present in the injectable particles in an amount ranging from 10% to 50% by weight, based on a total weight of the injectable particles.

In various embodiments, which may be used in conjunction with any of the preceding aspects and embodiments, the pH-altering agent may be released from the injectable particle by a mechanism selected from (a) diffusion from all or a portion of the injectable particles, (b) biodisintegration of all or a portion of the injectable particles, or (c) or a combination of (a) and (b).

In various embodiments, which may be used in conjunction with any of the preceding aspects and embodiments, the injectable particles may comprise a biostable core and a coating that comprises the pH-altering agent. The biostable core may, for example, be a hydrogel core. The biostable core may, for example, comprise one or more of methyl methacrylate monomer and vinyl alcohol monomer. In addition to the pH-altering agent, the coating may further comprise an additional material such as a binder material or a matrix material. In certain instances, the injectable particles may further comprise an additional coating that comprises poly[bis(trifluroethoxy)phosphazene].

In various embodiments, which may be used in conjunction with any of the preceding aspects and embodiments, the injectable particles may further comprise at least one therapeutic agent.

In various embodiments, which may be used in conjunction with any of the preceding aspects and embodiments, the injectable particles may further comprise at least one osmotic agent.

In other aspects of the present disclosure, injectable particles in accordance with any of the preceding aspects and embodiments may be provided in a container. In certain embodiments, the container may be a container that is configured for connection to a delivery catheter, for example, a syringe, among other possible containers.

In other aspects, the present disclosure pertains to methods of embolization which comprise administering injectable particles in accordance with any of the preceding aspects and embodiments into an intratumoral artery of a tumor. After administration, the pH-altering agent is released from the injectable particles such that a microenvironment of increased pH is created in a vascular bed of the tumor downstream of the injectable particles. For example, the pH of the microenvironment may be higher than a pH that would otherwise exist in the absence of the pH-altering agent (e.g., upon administering injectable particles of the same composition, except with the pH-altering agent removed).

In various embodiments, the pH-altering agent is released for a period of at least one hour after administering the injectable particles, for example, for a period ranging from 1 hour to 4 hours to 12 hours to 1 day to 2 days to 4 days to 1 week to 2 weeks to 4 weeks to 8 weeks (i.e., ranging between any two of the preceding numerical values) after administering the injectable particles, in certain cases, for a period ranging from 2 to 4 weeks after administering the injectable particles.

In various embodiments, the pH-altering agent is released in a manner that maintains the pH of the microenvironment at a value that is higher than a pH that would otherwise exist in the absence of the pH-altering agent (e.g., the pH that would exist in the microenvironment upon administering injectable particles of the same composition except with the pH-altering anent removed) for a period of at least one hour after administering the injectable particles, for example, for a period ranging from 1 hour to 4 hours to 12 hours to 1 day to 2 days to 4 days to 1 week to 2 weeks to 4 weeks to 8 weeks (i.e., ranging between any two of the preceding numerical values) after administering the injectable particles, in certain cases, for a period ranging from 2 to 4 weeks after administering the injectable particles.

Details of various aspects and embodiments of the invention are set forth in the description to follow. Other features and advantages of the invention will be apparent from the description and drawings, and from the claims.

DETAILED DESCRIPTION

The present disclosure pertains to injectable particles that comprise at least one pH-altering agent that is released in vivo at the site of action.

In certain embodiments, the injectable particles are configured to release an amount of the at least one pH-altering agent that is sufficient to at least temporarily maintain a microenvironment associated with the injectable particles at a pH that is higher than a pH that would otherwise exist in the absence of the injectable particles.

In certain embodiments, the injectable particles are designed such that, upon embolization of the intratumoral artery of the tumor with the injectable particles, the injectable particles release the at least one pH-altering agent in a manner such that a microenvironment is created in a vascular bed of the tumor downstream of the injectable particles. In various embodiments, the microenvironment has a pH that is higher (e.g., at least 0.2 pH units higher, preferably at least 0.5 pH units higher) than a pH that would otherwise exist in the microenvironment in the absence of the pH-altering agent (e.g., higher than a pH of a microenvironment created in the vascular bed of the tumor downstream of the injectable particles upon embolization with injectable particles of the same composition, except with the pH-altering agent removed). In certain of these embodiments, the injectable particles are configured to release the pH-altering agent in an amount that is sufficient to maintain the pH of the microenvironment at a value that is higher than the pH that would otherwise exist in the microenvironment in the absence of the pH-altering agent for a period of at least 1 hour up to 8 weeks or more, for example, ranging from 1 hour to 4 hours to 12 hours to 1 day to 2 days to 4 days to 1 week to 2 weeks to 4 weeks to 8 weeks (i.e., ranging between any two of the preceding numerical values), in certain instances, ranging from 2 to 4 weeks.

The injectable particles of the present disclosure may be used to treat various diseases and conditions in a variety of subjects. Subjects include vertebrate subjects, particularly humans and various warm-blooded animals, including pets and livestock. As used herein, "treatment" refers to the prevention of a disease or condition, the reduction or elimination of symptoms associated with a disease or condition, or the substantial or complete elimination of a disease or condition. Preferred treatments include embolization treatments.

In certain embodiments, injectable particles in accordance with the present disclosure may be used in TACE or TAE treatments. Because the injectable particles of the present disclosure comprise a pH-altering agent that is released in vivo, such particles may be useful in TACE and TAE procedures in which a tumor microenvironment is embolized by the injectable particles while at the same time providing controlled regulation of intratumoral pH though the release of the pH-altering agent in vivo. Without wishing to be bound by theory, it is hypothesized that the controlled regulation of pH within a tumor to basic pH will reduce or eliminate lactic acidosis effects, leading to higher glucose dependence and therefore increased tumor cell death, with the result being more effective TACE and TAE treatments.

The pH-altering agents for use in conjunction with the present disclosure include a wide variety of organic and inorganic pH-altering agents. In various embodiments, the pH-altering agents that are employed include (a) agents that are basic agents having a pH value (e.g., at pH value at 100 mM concentration in water at 25° C.) that is greater than 7.4, typically ranging from 7.5 to 10 (e.g., having a pH value ranging from 7.5 to 8.0 to 8.5 to 9.0 to 9.5 to 10) (meaning that a selected pH range can range between any two of the preceding values), (b) agents that are buffering agents having at least one pKa value (e.g., a pKa value extrapolated to infinite dilution (buffer concentration=0) in water at 25° C., also referred to as a pKa° value), greater than 7.6, typically ranging from 7.6 to 35 (e.g., having a pKa value ranging from 7.6 to 8.0 to 8.5 to 9.0 to 9.5 to 10 to 11 to 12 to 13 to 14 to 16 to 18 to 20 to 25 to 30 to 35) (meaning that a selected pKa range can range between any two of the preceding values) and (c) agents having both the pH value of (a) and the pKa value of (b).

Particular examples of inorganic pH-altering agents include carbonates, such as sodium carbonate (pH ~10.5, 25° C., 100 mM in $H_2O$), potassium carbonate (pH ~10.5, 25° C., 100 mM in $H_2O$) and calcium carbonate (pH ~9.9, 25° C., 100 mM in $H_2O$), and bicarbonates (also referred to as hydrogen carbonates), such as sodium bicarbonate (pH ~8.3, 25° C., 100 mM in $H_2O$) and potassium bicarbonate (pH ~8.3, 25° C., 100 mM in $H_2O$), among others. Carbonates act as buffering agents, and there are two pKa values, one for the bicarbonate <-> carbonic acid reaction and one for the bicarbonate <-> carbonate reaction. For sodium bicarbonate, the pKa for bicarbonate <-> carbonic acid reaction is ~6.4, and the pKa for bicarbonate <-> carbonate reaction is ~10.3.

Examples of inorganic pH-altering agents further include phosphates, including dibasic phosphates such as sodium phosphate dibasic (pH ~8.7-9.3, 25° C., 50 mg/mL in $H_2O$) or potassium phosphate dibasic (pH ~8.7-9.3, 25° C., 1 M in $H_2O$), among others. Phosphates acts as buffering agents, and there are three pKa values: one pKa for the phosphoric acid <-> monobasic reaction, one pKa for the monobasic <-> dibasic reaction and one pKa for the dibasic <-> tribasic reaction. For sodium phosphates, the pKa for the phosphoric acid <-> monobasic reaction is ~2.12, the pKa for the monobasic <-> dibasic reaction is ~7.21 and the pKa for the dibasic <-> tribasic reaction is ~12.67.

Examples of inorganic pH-altering agents further include phosphezene.

A variety of organic pH-altering agents may be used in conjunction with the present disclosure. In certain embodiments, one or more organic buffering agents are selected for use in the injectable particles. Suitable organic buffering agents may be selected, for example, from one or more of the following buffering agents, many of which are zwitterionic (each agent is listed along with reported pKa values at 25° C.): DIPSO (N,N-bis(2-hydroxyethyl)-3-amino-2-hydroxypropanesulfonic acid) (7.6), TAPSO (2-hydroxy-3-[tris(hydroxymethyl)methylamino]-1-propanesulfonic acid) (7.6), triethanolamine (7.8), N-ethyl morpholine (7.8), POPSO (piperazine-N,N'-bis(2-hydroxypropanesulfonic acid)) (7.8), HEPPSO (N-(2-hydroxyethyl)piperazine-N-(2-hydroxypropanesulfonic acid)) (7.9), HEPPS (4-(2-hydroxyethyl)piperazine-1-propanesulfonic acid) (8.0), Tricine (N-[tris(hydroxymethyl)methyl]-glycine) (8.1), Tris (tris(hydroxymethyl)aminomethane) (8.1), glycinamide (8.1), glycylglycine (8.3), HEPBS (N-(2-hydroxyethyl)piperazine-N'-(4-butanesulfonic acid)) (8.3), bicine (N,N-bis(2-hydroxyethyl)glycine) (8.3), TAPS (N-[tris(hydroxymethyl) methyl]-3-aminopropanesulfonic acid) (8.4), morpholine (8.5), N-methyldiethanolamine (8.5), AMPD (2-amino-2-methyl-1,3-propanediol) (8.8), diethanolamine (8.8), AMPSO (N-(1,1-dimethyl-2-hydroxyethyl)-3-amino-2-hydroxypropanesulfonic acid) (9.1), CHES (2-(cyclohexylamino)-1-ethanesulfonic acid) (9.4), ethanolamine (9.5), AMP (2-amino-2-methyl-1-propanol) (9.7), piperazine (9.7), glycine (9.8), CAPSO (9.8), 1,3-diaminopropane (10.3), CAPS (3-(cyclohexylamino)-1-propanesulfonic acid) (10.5), CABS (4-(cyclohexylamino)-1-butanesulfonic acid) (10.7), and piperidine (11.1), as well as pharmaceutically acceptable salts thereof, where applicable.

The preceding compounds are also typically basic agents as well.

As previously noted, the present disclosure pertains to injectable particles that release one or more pH-altering agents (e.g., selected from those discussed above, among others) in vivo.

The pH-altering agents may be released via any suitable mechanism including (a) by diffusion from all or a portion of the injectable particle (e.g., where all of the injectable particle or a portion of the injectable particle corresponds to a matrix that contains the pH-altering agent and from which the pH-altering agent diffuses), (b) by biodisintegration (e.g., by dissolution and/or biodegradation) of all or a portion of the injectable particle (e.g., where all of the injectable particle or a portion of the injectable particle (i)

contains the pH-altering agent and (ii) is dissolved and/or biodegraded in vivo such that the pH-altering agent is released), or a combination of the foregoing, among other possible mechanisms.

Typically, one or more pH-altering agents are present in the injectable particles in an amount ranging from 1% to 90%, more typically, from 10% to 50% by weight, based on the total weight of the injectable particles.

The injectable particles of the present disclosure may vary widely in shape, In certain embodiments, they are spherical (ball-shaped).

The injectable particles of the present disclosure may vary significantly in size, with typical diameters ranging, for example, from 25 microns (μm) or less to 5000 microns or more, for example, ranging from 25 microns to 50 microns to 75 microns to 100 microns to 150 microns to 250 microns to 500 microns to 750 microns to 1000 microns to 1500 microns to 2000 microns to 2500 microns to 5000 microns (i.e., including all ranges spanning any two of the preceding values). Where collections of injectable particles are employed, at least 95 vol % of the population may fall within these ranges.

The injectable particles of the present disclosure may be biostable, biodisintegrable (e.g., dissolved and/or biodegraded in vivo), or partially biostable and partially biodisintegrable (e.g., where an injectable particle comprises a biostable core and a coating layer that is/are dissolved and/or biodegraded in vivo). As used herein a particle or a portion thereof is "biodisintegrable" if it loses quantifiable mass. This process can occur in the range of hours to days to weeks to months to years. The degradation mechanism can result from mass or molecular weight loss. As used herein a particle or a portion thereof is "biostable" if it is not "biodisintegrable". In certain instances, the particle or a portion thereof is "biostable" if it remains present in the vasculature for at least 1 year, and preferably at least 5 years.

The injectable particles and portions thereof (e.g., cores, coatings, etc.) in accordance with the present disclosure may be formed using a variety of inorganic materials (e.g., glasses, ceramics, metals, etc.), organic materials (e.g., non-polymeric organic compounds, polymers, etc.), as well as combinations of inorganic and organic materials.

In various beneficial embodiments, injectable particles and portions thereof (e.g., cores, coatings, etc.) in accordance with the present disclosure may be formed using a variety of polymers, which may be biostable or hiodisintegrable. Biodisintegrable polymers include polymers that biodegrade in vivo and polymers that dissolve in vivo. As used herein a "biodegradable polymer" is one that undergoes chain cleavage in vivo.

The injectable particles of the invention may be non-crosslinked or they may be covalently and/or non-covalently crosslinked. Thus, in some embodiments, crosslinking agents such as covalent crosslinking agents or ionic crosslinking agents may be present in the injectable particles, whereas in other embodiments crosslinking agents are absent from the particles.

Suitable organic materials for forming the injectable particles and portions thereof (e.g., cores, coatings, etc.) may be selected, for example from one or more of the following materials, many of which are polymers: polyphosphazines including poly[bis(trifluroethoxy)phosphazene] and poly[bis(ethyl alanato)phosphazene]; homopolymers and copolymers of vinyl monomers including vinyl alcohol homopolymers and copolymers, which may be acetalized (e.g., copolymers of vinyl alcohol and acrylic acid and salts thereof, copolymers of vinyl alcohol and 2-acrylamido-2-methylpropane sulfonic acid and salts thereof, etc.), polyvinyl ketones, polyvinylcarbazoles, polyvinyl esters such as polyvinyl acetates, polyvinyl halides such as polyvinyl chlorides, ethylene-vinyl acetate copolymers (EVA), polyvinylidene chlorides, polyvinyl ethers such as polyvinyl methyl ethers, polyvinylpyrrolidone, vinyl aromatics such as polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk); silicone polymers and copolymers; poly(carboxylic add) polymers and copolymers including polyacrylic and polymethacrylic add homopolymers and copolymers, as well as salts thereof, ethylene-methacrylic add copolymers and ethylene-acrylic add copolymers, where some of the add groups can be neutralized with either zinc or sodium ions (commonly known as ionorners); acrylate and methacrylate polymers and copolymers (e.g., copolymers of methyl methacylate and triethylene glycol dimethacrylate); acetal polymers and copolymers; ketal polymers and copolymers (e.g., poly(1,4-phenylene-acetonedimethylene ketal), poly(cyclohexane-1,4-diylacetone dimethylene ketone, etc.); polyimines; polyhydrazones; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polyamide polymers and copolymers including nylon 6,6, nylon 12, polycaprolactarns, polyacrylamides and polyether block amides; polysulfone polymers and copolymers including polyarylsulfones and polyethersulfones; resins including alkyd resins, phenolic resins, urea resins, melamine resins, epoxy resins, allyl resins and epoxide resins; polycarbonates; polyacrylonitriles; polybenzimidazoles; polyesters including polyethylene terephthalates and aliphatic polyester polymers and copolymers of alpha-hydroxy acids such as polylactide (including d-, l- and meso forms), polyglycolide and poly(lactide-co-glycolide), epsilon-caprolactone, poly(lactide-co-caprolactone), polyhydroxybutyrate, polyhydroxyyalerate, poly(para-dioxanone), polymers of trimethylene carbonate (and its alkyl derivatives), 1,4-dioxepan-2-one, 1,5-dioxepan-2-one, and 6,6-dimethyl-1,4-dioxan-2-one; polyether polymers and copolymers including polyarylethers such as polyphenylene ethers, polyether ketones, polyether ether ketones, and polyalkyl oxides such as polyethylene oxide (PEO) and polypropylene oxide; polyphenylene sulfides; polyisocyanates; polyolefin polymers and copolymers, Including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); thermoplastic polyurethanes (TPU); elastomers such as elastomeric polyurethanes and polyurethane copolymers (including block and random copolymers that are polyether based, polyester based, polycarbonate based, polyisobutylene based, aliphatic based, aromatic based and mixtures thereof; p-xylylene polymers; polyiminocarbonates; copoly(ether-esters) such as polyethylene oxide-polylactic add copolymers; polyalkylene oxalates; polyoxaamides and polyoxaesters (including those containing amines and/or amido groups); polyorthoesters; waxes, such as paraffin wax; biopolymers, such as polypeptides, proteins and polysaccharides and fatty adds (and esters thereof), including gelatin, starch, collagen, dextranomer, fibrin, fibrinogen, elastin, alginic add, chitosan, glycosaminoglycans such as hyaluronic add, as well as mixtures of the preceding.

In certain embodiments where biodegradable polymers are employed, it may be desirable to employ biodegradable polymers having non-acidic breakdown products. Examples of biodegradable polymers that have been reported to have non-acidic breakdown products include polyacetals, polyketals (e.g., poly(1,4-phenylene-acetonedimethylene ketal), poly(cyclohexane-1,4-diylacetone dimethylene ketone, etc.), polyphosphazenes (e.g., poly[bis(ethyl alanato)phosphazene], etc.), polyimines, polyhydrazones, and polyorthoesters, among others.

In certain embodiments the injectable particles may comprise one or more coatings surrounding a core, at least one of which contains the pH-altering agent. Such coatings containing pH-altering agents may consist largely of the pH-altering agent (e.g., may contain at least 90 wt %, at least 95 wt % or at least 99 wt % of the pH-altering a gent) or may contain the pH-altering agent admixed with one or more additional materials, such as binders and matrix materials, which may be selected, for example, from small molecule organic compounds, biostable polymers and biodisintegrable polymers.

In some embodiments, a known injectable particle may be coated with a coating that contains one or more pH-altering agents. Examples of such injectable particles include various polymer-based microspheres that are employed to embolize blood vessels. Specific examples include vinyl alcohol based microspheres, including acetalized polyv alcohol microspheres (e.g., Contour SE™), microspheres formed from copolymers of vinyl alcohol and acrylic add and salts thereof (e.g., QuadraSphere®), microspheres formed from copolymers of vinyl alcohol and 2-acrylamido-2-methylpropane sulfonic acid and salts thereof) (e.g., Bead Block™), microspheres formed from tris-acryl cross-linked with gelatin (e.g., Embosphere®), and microspheres including hydrogel cores comprising methyl methacylate coated with poly[bis(trifiuroethoxy)phosphazene] (e.g., Embozene®), among others.

In some embodiments, the injectable particles of the present disclosure comprise osmotic agents. Such agents may be added to increase osmotic pressure in the hydration layer associated with the particle, which will increase release of the pH-altering agent(s) from the particle, thereby improving penetration of the pH-altering agents including buffering agents into tumor tissue. Where present, the injectable particles may comprise osmotic agents in an amount ranging from 5% to 40%, based on the total weight of the injectable particles.

Examples of osmotic agents include inorganic salts such as sodium chloride, potassium chloride, sodium phosphate and potassium phosphate, among others, and organic osmotic agents including sugars such as fructose, sucrose, dextrose and lactose, among others, sugar alcohols such as ethylene glycol, xylitol, sorbitol and mannitol, among others, amino acids such as l-arginine, among others, as well as combinations thereof.

In some embodiments, the injectable particles of the present disclosure may comprise one or more therapeutic agents. Where present, the injectable particles may comprise therapeutic agents in an amount ranging from 0.0001% to 25% (e.g., an amount ranging from 0.0001% to 0.001% to 0.01% to 0.1% to 1% to 5% to 10% to 15% to 20% to 25%) (meaning that a selected amount can range between any two of the preceding values), based on the total weight of the injectable particles.

Examples of therapeutic agents which may be used in the compositions of the invention for embolic applications include toxins (e.g., ricin toxin, radioisotopes, or any other agents able to kill undesirable cells, such as those making up cancers and other tumors such as uterine fibroids) and agents that arrest growth of undesirable cells.

Specific examples of therapeutic agents may be selected from suitable members of the following: antineoplastic/antiproliferative/anti-miotic agents including antimetabolites such as folic acid analogs/antagonists (e.g., methotrexate, etc.), purine analogs (e.g., 6-mercaptopurine, thioguanine, cladribine, which is a chlorinated purine nucleoside analog, etc.) and pyrimidine analogs (e.g., cytarabine, fluorouracil, etc.), alkaloids including taxanes (e.g., paclitaxel, docetaxel, etc.), alkylating agents such as alkyl sulfonates, nitrogen mustards (e.g., cyclophosphamide, ifosfamide, etc.), nitrosoureas, ethylenimines and methylmelamines, other aklyating agents (e.g., dacarbazine, etc.), antibiotics and analogs (e.g., daunorubicin, doxorubicin, idarubicin, mitomycin, bleomycins, plicamycin, etc.), platinum complexes (e.ag, cisplatin, carboplatin, etc.), antineoplastic enzymes (e.g., asparaginase, etc.), agents affecting microtubule dynamics (e.g., vinblastine, vincristine, colchicine, Epo D, epothilone), caspase activators, proteasome inhibitors, angiogenesis inhibitors (e.g, statins such as endostatin, cerivastatin and angiostatin, squalamine, etc.), rapamycin (sirolimus) and its analogs (e.g., everolimus, tacrolimus, zotarolimus, etc.), etoposides, and many others (e.g., hydroxyurea, flavopiridol, procarbizine, mitoxantrone, campothecin, etc.), various pharmaceutically acceptable salts and derivatives (e.g., esters, etc.) of the foregoing, and combinations of the foregoing, among other agents. Further examples of therapeutic agents include radioisotopes including $^{90}Y$, $^{32}P$, $^{18}F$, $^{140}La$, $^{153}Sm$, $^{165}Dy$, $^{166}Ho$, $^{169}Er$, $^{169}Yb$, $^{177}Lu$, $^{186}Re$, $^{188}Re$, $^{103}Pd$, $^{198}Au$, $^{192}Ir$, $^{90}Sr$, $^{111}In$ or $^{67}Ga$, as well biologic agents such as immunotherapy antibodies or other biological components.

In some embodiments, the injectable particles of the present disclosure comprise agents that increase radiopacity of the microparticles (i.e., making the polymer more absorptive of x-rays and thus more visible under x-ray imaging techniques such as x-ray fluoroscopy, among others). Examples of radiopacifying agents include metals, metal salts and metal oxides, and iodinated compounds. More specific examples of such agents include gold, tungsten, platinum, tantalum, iridium, or other dense metal, barium sulfate, bismuth subcarbonate, bismuth trioxide, bismuth oxychloride, metrizamide, iopamidol, iothalamate sodium, iodomide sodium, and meglumine. Where present, the injectable particles may comprise radiopacifying agents in an amount ranging from 0.01% to 40%, based on the total weight of the injectable particles.

Injectable particle compositions in accordance with the present disclosure may be stored and transported in a sterile dry form. The dry composition may be shipped, for example, in a catheter, syringe, vial, ampoule, or other container (e.g., any container that is configured to interact with a delivery catheter), and it may be mixed with a suitable liquid carrier (e.g. sterile water for injection, physiological saline, phosphate buffer, a solution containing an imaging contrast agent, etc.) prior to administration. In this way the concentration of the composition to be injected may be varied at will, depending on the specific application at hand, as desired by the health care practitioner in charge of the procedure. One or more containers of liquid carrier may also be supplied and shipped, along with the dry particles, in the form of a kit.

In other embodiments, the injectable particles may be stored in a sterile suspension that includes water and the injectable particles. As above, the suspension may be stored, for example, in a catheter, syringe, vial, ampoule, or other container. The suspension may also be mixed with a suitable liquid carrier (e.g. sterile water for injection, physiological saline, phosphate buffer, a solution containing contrast agent, etc.) prior to administration, allowing the concentration of administered particles in the suspension to be reduced prior to injection, if so desired by the health care practitioner in charge of the procedure. One or more containers of liquid carrier may also be supplied to form a kit.

The present invention encompasses various ways of administering the injectable particles of the invention to effect embolization or another procedure benefiting from the injectable particles of the present disclosure. One skilled in the art can determine the most desirable way of administering the particles, depending on the type of treatment and the condition of the patient, among other factors. Methods of administration include, for example, percutaneous techniques as well as other effective routes of administration. For example, the particulate compositions of the invention may be delivered through a syringe or through a catheter, for instance, a microcatheter, which can be advanced over a guidewire, a steerable microcatheter, or a flow-directed microcatheter, among other devices.

Example 1

A coating of pH-altering agent is spray coated onto a surface of an embolic microsphere to provide microspheres with slow release of a pH-altering agent. In a particular embodiment, diethanolamine is dissolved in isopropyl alcohol and sprayed onto a surface of Embozene® embolic microspheres such that the diethanolamine is present on the microspheres in an amount ranging from 10 wt % to 50 wt %, based on a total weight of the coated microspheres. The microspheres may then be dried in a vacuum oven to remove excess solvent. If desired, such microspheres may be diluted with a suitable solution (e.g., saline solution or contrast solution) to a dilution of 2×, 5×, 10×, 20× or more by volume, or such microspheres may be subsequently diluted with a suitable solution (e.g., saline solution or contrast solution) at a time of administration to a patient.

Example 2

Microparticles are formed as described in Example 1, except that an osmotic agent, specifically dextrose, is added to the coating solution such that the osmotic agent is present on the microspheres in an amount ranging from 0.001 wt % to 5 wt %, based on a total weight of the coated microspheres.

We claim:

1. Injectable particles comprising:

a biostable core; and a coating comprising at least one pH-altering agent that is configured to be released from the injectable particles in vivo upon embolization of an intratumoral artery of a tumor with the injectable particles, wherein the at least one pH-altering agent includes a basic agent having a pH of 7.5 or more and a buffering agent having a pKa value of 7.6 or more, and the pH-altering agent includes at least one of a carbonate, a bicarbonate, and a phosphate, wherein the pH-altering agent is configured to be released from the injectable particle by a mechanism selected from (a) diffusion from all or a portion of the injectable particles, (b) biodisintegration of a portion of the injectable particles wherein the injectable particles further comprise a biodisintegrable polymer, or (c) or a combination of (a) and (b).

2. The injectable particles of claim 1, wherein the injectable particles are configured such that, upon embolization of the intratumoral artery of the tumor with the injectable particles, the injectable particles release the pH-altering agent such that a microenvironment is created in a vascular bed of the tumor downstream of the injectable particles that has a pH that is higher than a pH that would otherwise exist in the absence of the pH-altering agent.

3. The injectable particles of claim 1, wherein the injectable particles are spherical particles.

4. The injectable particles of claim 1, wherein the injectable particles range from 20 to 1500 microns in diameter.

5. The injectable particles of claim 1, wherein the pKa value is in a range of 7.6 to 35.

6. The injectable particles of claim 1, wherein the pH-altering agent further comprises an organic compound.

7. The injectable particles of claim 1, wherein the pH-altering agent is present in the injectable particles in an amount ranging from 10% to 50% by weight, based on a total weight of the injectable particles.

8. The injectable particles of claim 1, wherein the biostable core is a hydrogel core.

9. The injectable particles of claim 1, wherein the biostable core comprises a polymer that comprises one or more of methyl methacrylate monomer and vinyl alcohol monomer.

10. The injectable particles of claim 1, wherein the injectable particles further comprise an additional coating that comprises poly [bis (trifluroethoxy) phosphazene].

11. The injectable particles of claim 1, wherein the coating further comprises a binder material or a matrix material.

12. The injectable particles of claim 1, wherein the injectable particles further comprise at least one therapeutic agent.

13. The injectable particles of claim 1, wherein the injectable particles further comprise at least one osmotic agent in an amount ranging from 5% to 40%, based on a total weight of the injectable particles.

14. The injectable particles of claim 2, wherein the microenvironment is created in a vascular bed of the tumor downstream of the injectable particles that has a pH that is 0.2 pH units higher than a pH that would otherwise exist in the absence of the pH-altering agent.

15. The injectable particles of claim 2, wherein the microenvironment is created in a vascular bed of the tumor downstream of the injectable particles that has a pH that is 0.5 pH units higher than a pH that would otherwise exist in the absence of the pH-altering agent.

16. The injectable particles of claim 1, wherein the injectable particles further comprise an agent that increases radiopacity of the injectable particles.

17. The injectable particles of claim 1, further comprising an osmotic agent of dextrose in an amount ranging from 0.001 wt % to 5 wt %, based on a total weight of the injectable particles.

* * * * *